United States Patent
Buchbinder et al.

(10) Patent No.: US 9,283,021 B2
(45) Date of Patent: *Mar. 15, 2016

(54) PLAQUE STABILIZATION USING CRYOENERGY

(71) Applicant: Cryotherapeutics GmbH, Postdam (DE)

(72) Inventors: Maurice Buchbinder, La Jolla, CA (US); Randell Louis Werneth, San Diego, CA (US); Yiannakis Petrou Yianni, Hants (GB); J. Christopher Flaherty, Auburndale, FL (US); Daniel Nahon, Ottawa (CA); Domenic Santoianni, Kirkland (CA)

(73) Assignee: Cryotherapeutics GmbH, Cologne (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/600,416

(22) Filed: Jan. 20, 2015

(65) Prior Publication Data

US 2015/0133905 A1    May 14, 2015

Related U.S. Application Data

(63) Continuation of application No. 13/446,189, filed on Apr. 13, 2012, now Pat. No. 8,968,282.

(60) Provisional application No. 61/474,987, filed on Apr. 13, 2011.

(51) Int. Cl.
*A61B 18/18*    (2006.01)
*A61B 18/02*    (2006.01)
(Continued)

(52) U.S. Cl.
CPC .................. *A61B 18/02* (2013.01); *A61F 7/123* (2013.01); *A61B 2018/0022* (2013.01);

(Continued)

(58) Field of Classification Search
CPC ..................... A61B 18/02; A61B 2018/00005; A61B 2018/00011; A61B 2018/00023; A61B 2018/00035; A61B 2018/00047; A61B 2018/0022; A61B 2018/00232; A61B 2017/00778; A61B 2017/22; A61B 2017/22012; A61B 2017/02
See application file for complete search history.

(56) References Cited

U.S. PATENT DOCUMENTS

| 6,602,246 B1 | 8/2003 | Joye et al. | 606/21 |
| 7,081,112 B2 | 7/2006 | Joye et al. | 606/21 |

(Continued)

FOREIGN PATENT DOCUMENTS

| WO | WO 9852479 | 11/1998 | A61B 17/36 |
| WO | WO 9927862 | 6/1999 | A61B 17/36 |

(Continued)

OTHER PUBLICATIONS

European Patent Office, International Search Report, PCT/GB2012/050820, date of mailing Jun. 12, 2012, 4 pages.

*Primary Examiner* — Robert N Wieland
(74) *Attorney, Agent, or Firm* — Sunstein Kann Murphy & Timbers LLP

(57) ABSTRACT

There is provided a method of supplying cryoenergy to a plaque within a blood vessel. The method comprises expanding an expandable membrane of a catheter apparatus with a pressure of less than 5 ATM (507 kPa), the catheter apparatus having been placed in thermal contact with the plaque within the blood vessel. The method also comprises establishing a temperature of between +15° C. (288K) and −35° C. (238K) at an interface of the expandable membrane and the blood vessel. A system and catheter apparatus are also provided.

23 Claims, 10 Drawing Sheets

(51) Int. Cl.
  *A61F 7/12* (2006.01)
  *A61B 18/00* (2006.01)

(52) U.S. Cl.
  CPC .......... *A61B 2018/0041* (2013.01); *A61B 2018/00345* (2013.01); *A61B 2018/00791* (2013.01); *A61B 2018/0212* (2013.01); *A61B 2018/0237* (2013.01); *A61B 2018/0262* (2013.01); *A61F 2007/126* (2013.01)

(56) References Cited

U.S. PATENT DOCUMENTS

| | | | |
|---|---|---|---|
| 2003/0149368 A1 | 8/2003 | Hennemann et al. | 600/483 |
| 2004/0133256 A1 | 7/2004 | Callister | 607/105 |
| 2004/0199229 A1 | 10/2004 | Lasheras | 607/105 |
| 2007/0093710 A1 | 4/2007 | Maschke | 600/407 |
| 2007/0185445 A1 | 8/2007 | Nahon et al. | 604/96.01 |
| 2010/0049184 A1 | 2/2010 | George et al. | 606/21 |
| 2011/0054452 A1 | 3/2011 | Chun | 606/21 |
| 2013/0103019 A1* | 4/2013 | Joye | A61B 18/02 606/21 |

FOREIGN PATENT DOCUMENTS

| | | | |
|---|---|---|---|
| WO | WO 9938934 | 8/1999 | C10B 45/02 |
| WO | WO 0054684 | 9/2000 | A61B 18/18 |
| WO | WO 0164145 A1 | 9/2001 | A61F 7/00 |
| WO | WO 0207625 A2 | 1/2002 | A61B 18/02 |
| WO | WO 0207628 A2 | 1/2002 | A61B 18/18 |
| WO | WO 0239080 A1 | 5/2002 | G01K 13/00 |
| WO | WO 02083196 A2 | 10/2002 | |
| WO | WO 03028524 A3 | 4/2003 | A61B 18/18 |
| WO | WO 03039338 | 5/2003 | |
| WO | WO 2004049918 A2 | 6/2004 | |
| WO | WO 2006065610 A2 | 6/2006 | A61B 18/02 |
| WO | WO 2010081062 A1 | 7/2010 | A61B 18/02 |
| WO | WO 2011014812 A1 | 2/2011 | A61B 18/02 |

* cited by examiner

PLAQUE STABILIZATION USING CRYOENERGY

This application is a continuation of co-pending U.S. patent application Ser. No. 13/446,189, filed Apr. 13, 2012, now issued as U.S. Pat. No. 8,968,282, which in turn claimed priority from U.S. Provisional Patent Application 61/474,987, filed Apr. 13, 2011, both of which are incorporated herein by reference in their entireties.

TECHNICAL FIELD

The present invention relates to use of cryoenergy in cardiovascular systems.

BACKGROUND ART

From the late 1970s, cryoenergy has been used in the cardiovascular system starting from, for example, 1977 when it was used to surgically treat cardiac arrhythmias. Over the ensuing years it became widely recognized that cryoenergy was the energy source of choice when working in the heart. Its safety and efficacy was unsurpassed as surgeons were able to ablate delicate cardiac structures such as the A-V node, pulmonary veins and delicate peri-nodal atrial tissue without concern for thrombosis, perforation or other adverse events.

More recently, researchers have started investigating the use of cryoenergy in the vascular system as a method to treat calcified plaque. Clinical data published by Laird et. al. "Cryoplasty for the Treatment of Femoropopliteal Arterial Disease: Extended Follow-up Results" J ENDOVASC THE 2006; 13 (Suppl II): II-52-II-59 has shown that cryoenergy achieves good clinical results when used in highly stenosed vessels of the peripheral vasculature.

Much of this previous work has been in treating calcified plaque in patients with calcified highly stenosed vessels (>70% stenosis) as an alternative to drugs, balloon angioplasty, stents or other conventionally used therapies.

Cryoenergy is typically applied to a vessel using a balloon based catheter, in which a refrigerant is used to expand a balloon into contact with a target. The temperatures used in treating such calcified highly stenosed blood vessels range from −10° C. to −20° C. (263K to 253K) and are generally warmer than those used in the ablation field (such as those used to treat arrhythmia or for cancer tumor ablation) where refrigerant temperatures will generally be colder than −70° C. (203K). Typically, the pressure in the balloon will be above 5 atmospheres (ATM), 507 kPa, as the goal of the therapy is to force open critically stenosed calcified vessels.

There has also been some interest in using cryoenergy on non-critically stenosed plaque typical of so called vulnerable or unstable plaque, as exemplified by U.S. Pat. Nos. 6,673,066, 6,602,246 and 6,955,174. Vulnerable plaque, or unstable plaque, may be defined as a non-flow limiting plaque which is lipid rich with a thin cap fibroatheroma. For the purposes of this document the terms vulnerable and unstable plaque are used interchangeably.

When these plaques rupture, a thrombus forms and causes a heart attack. A discussion, description and characteristics of these types of plaques is reviewed in Libby, "Atherosclerosis: The New View" Scientific American, May 2002, pg. 47. In some early work, the biological effect was poorly understood and improperly described as, for example, in U.S. Pat. No. 6,955,174 where cryotherapy treatment is described which "inhibits release of the retained fluid into the blood vessel". It is now thought that this mechanism is incorrect and that a ruptured plaque does not release materials into the bloodstream but causes a thrombus to form at the site of rupture. This mechanism is described by Muller, "Presentation at Cardiovascular Revascularization Therapies", Mar. 28-31, 2005, Washington D.C., and by Fuster et al, "Atherothrombosis and High Risk Plaque", Journal of the American College of Cardiology, 2005, Vol. 46, No. 6, pp. 937-54.

There is currently no effective cryoenergy based method to treat unstable plaque that has or is likely to rupture.

Many of the known cryocatheters have safety limitations. Typically, the catheter will use a phase change Joule Thomson refrigerant system in which liquid refrigerant transforms into a gas which inflates the catheter balloon. This system carries with it an inherent risk of gas leakage causing serious harm or death due to emboli. A typical device with such inherent risks is described in U.S. Pat. No. 6,908,462.

Additionally, the catheter in many devices employs a double balloon structure which causes an increase in bulk and diameter compared to smaller designs. The double balloon structure is used to place insulation between the balloons in order to achieve a correct target temperature, as is described in U.S. Pat. No. 6,514,255. A double balloon structure may also be used to mitigate safety concerns caused from gas leaks such as those described above. The increase in bulk and diameter makes the double balloon type design more difficult to develop a clinically acceptable design for small diameter arteries such as in the coronary or smaller peripheral vasculature where the catheter will be difficult to manoeuver.

As described above, conventional cryotreatment for cardiovascular diseases has been aimed at cryoplasty, preventing restenosis of the vessel or treating atrial fibrillation. These methods typically use a double walled balloon at a high pressure, usually to dilate the target vessel. $N_2O$ is typically used as a refrigerant which undergoes a phase change. The high pressure serves to dilate the vessel and the pressure also controls the boiling point of the refrigerant inside the inner balloon thereby to control the temperature of the $N_2O$. There is currently no effective cryoenergy based method to treat unstable plaque that has or is likely to rupture.

SUMMARY OF THE INVENTION

According to a first aspect of the present invention, there is provided a method of supplying cryoenergy to a plaque within a blood vessel, comprising: expanding an expandable membrane of a catheter apparatus with a pressure of less than 5 ATM (507 kPa), the catheter apparatus having been placed in thermal contact with the plaque within the blood vessel; and, establishing a temperature of between +15° C. (288K) and −35° C. (238K) at an interface of the expandable membrane and the blood vessel.

The present invention delivers cryoenergy to a vulnerable plaque that has ruptured, or is likely to rupture, at the surface of a blood vessel in order to modify the plaque structure, i.e. the plaque morphology will change from an unstable to a more stable state, such that healing is aided and the associated risk of thrombus formation is minimised or eliminated.

Pressures used in conventional cryocatheters to treat stenotic vessels are typically higher than 5 ATM (507 kPa) such that they may be dangerous to use. The application of high pressure cryo-energy to an unstable plaque may induce a cellular hyperplasia reaction that leads to subsequent stenosis and, in the short term, an undesirable and potentially dangerous blockage. By using low pressures, the present invention mitigates the risks of cryotherapy and causes a change in the plaque morphology to aid in healing.

The temperature range utilised in the present invention is such that cell ablation is moderated during the process, unlike many conventional cryocatheter systems where the aim is to ablate the cells. The range ensures a sufficient amount of cryoenergy is delivered to the plaque for effective morphology changes to occur whilst moderating ablation.

The catheter apparatus may have a single expandable membrane. The catheter apparatus is thus significantly more manoeuvrable and streamlined than known catheters having multiple membranes without compromising on safety due to any liquid refrigerant, in fact, catheter safety is increased. Moreover, the simpler catheter design to those conventional designs employing a double balloon system to mitigate leakage risks, or any other design to do the same, is particularly advantageous as it is inherently simpler and therefore reduces costs and manufacturing complexity.

The expandable membrane may be compliant with the blood vessel such that, when in place, damage to the vulnerable plaque is minimised and a good fit with the target area is ensured for effective heat transfer and a more even temperature distribution around the plaque. The expandable membrane may also be semi-compliant or non-compliant depending on the required application. The expandable membrane may have a substantially smooth exterior surface to provide an intimate contact and thereby further improve the heat transfer properties.

The method may also further comprise determining expandable membrane characteristics using a sensor provided with the catheter apparatus. The characteristics of the expandable membrane can thus be monitored, for example, temperature or pressure or both.

The method may further comprise imaging the catheter apparatus, wherein the expandable membrane comprises a radio opaque substance. The catheter apparatus can thus be imaged and tracked for, for example, effective positioning of the catheter in the vessel or safety monitoring.

The expandable membrane is preferably expanded with a pressure of less than 4 ATM (405 kPa), more preferably expanded with a pressure of less than 3 ATM (304 kPa), even more preferably expanded with a pressure of less than 2 ATM (203 kPa) and alternatively expanded with a pressure of less than or approximately equal to 1 ATM (101 kPa). In this way, the risk of plaque rupture and subsequent stenosis when cryoenergy is applied to vulnerable plaque is significantly reduced while effectively modifying plaque structure through the supply of cryoenergy such that it is stabilised or eliminated.

The expandable membrane may be configured to contain refrigerant and the act of establishing a temperature may comprise supplying refrigerant to the expandable membrane.

Further, refrigerant inside the expandable membrane may be maintained in a liquid state and thus the refrigerant does not undergo a phase change or expansion i.e. there is no endothermic evaporation or Joule Thomson effect. This mitigates the risk of gas leakage in the apparatus.

Refrigerant and/or other material, for example, other cooling components, inside the expandable membrane may be maintained at a temperature of between −25° C. (248K) and −55° C. (218K) in order to safely and effectively transfer the required heat from the vulnerable plaque for plaque morphology changes to occur.

Further, the refrigerant may comprise a perfluorocarbon. In this way, the safety of the method is enhanced. The perfluorocarbon remains in a relatively low viscosity liquid state, preferably less than 10 cSt over a temperature range of +37° C. to −85° C. This makes it easier to pump at cold temperatures. Additionally, because it remains in a liquid state, it is inherently safer in the case of a leak in the catheter apparatus, since the refrigerant will not vaporise and cause a gas emboli in the bloodstream. Moreover, it is biocompatible in the case of a leak.

The method may also further comprise determining refrigerant characteristics using a sensor provided with the catheter apparatus. The characteristics of the refrigerant can thus be monitored, for example, temperature or pressure or both.

The method may also comprise determining a state of occlusion of the blood vessel using a temperature sensor provided with the catheter apparatus. There may be more than one temperature sensor on the surface of the expandable membrane. In this manner a temperature profile or map around the expandable membrane may be determined. This could be useful in determining 'hot' or 'cold' spots which could then be used in the control of the refrigerant flow. Furthermore, one or more temperature readings, either in space or time, could be used to determine the state of blood flow between the expandable member and the vessel wall. It is known that when occlusion occurs the thermal load will greatly decrease since the blood flow ceases thereby causing a more rapid temperature drop. Since occlusion time is an important parameter to the physician and since the rate of temperature drop at a constant refrigerant flow is an indication of occlusion, the rate of temperature drop can be a useful feature to indicate when occlusion has occurred or the reverse when the vessel has been reopened following cryotreatment.

The method may also further comprise imaging the refrigerant, wherein the refrigerant comprises a radio opaque substance. The refrigerant can thus be imaged and tracked for, for example, effective positioning of the catheter in the vessel or safety monitoring.

Alternatively, the act of establishing a temperature may comprise activating an endothermic reaction thus avoiding the need for a refrigerant. Moreover, the endothermic reaction may be activated by pressurising the expandable member. The endothermic reaction may be activated by expanding the expandable member.

Further, the endothermic reaction may be a reaction between one or more of the following pairs of compounds: water and ammonium nitrate; water and ammonium chloride; barium hydroxide octahydrate crystals and dry ammonium chloride; water and ammonium chloride; thionyl chloride and cobalt(II) sulphate heptahydrate; water and potassium chloride; water and ammonium thiocyanate; ethanoic acid and sodium carbonate; and combinations thereof.

Alternatively, the temperature within the expandable membrane may be maintained by a cooling element positioned proximate to the expandable membrane thus avoiding the need for a refrigerant. Moreover, the cooling element comprises a thermoelectric cooling element. The cooling element may comprise a Peltier component.

According to another aspect of the invention there is provided a system comprising: a catheter apparatus, the catheter apparatus having an expandable membrane; a pressure regulator configured to regulate the expansion of the expandable membrane such that the expandable membrane is expanded with a pressure of less than 5 ATM (507 kPa); and, a cooling element configured to establish a temperature of between +15° C. (288K) and −35° C. (238K) at an interface between the expandable membrane and a blood vessel when the catheter apparatus has been placed in the blood vessel. The cooling element may be selected from the group consisting of: a refrigerant; endothermic reaction components; a thermoelectric cooling element such as a Peltier element; and combinations of these. A temperature controller may be included to provide closed loop temperature monitoring, such as a controller including a temperature sensor wherein the controller is configured to monitor temperature and adjust the cooling element to maintain the interface temperature between +15° C. (288K) and −35° C. (238K).

Further, the expandable membrane may be configured to contain fluid, the system further comprising a fluid supply for supplying fluid to the expandable membrane and wherein the pressure regulator is configured to regulate the pressure of the fluid supply such that the expandable membrane is expanded with a pressure of less than 5 ATM (507 kPa). The fluid may be saline or refrigerant or other suitable fluid for expanding the membrane.

The system may further comprise a vacuum pump positioned in a return line between the expandable membrane and a fluid reservoir. The system may also comprise a connection apparatus adapted to cool a refrigerant supply line by a separate refrigerant line from the fluid supply.

According to another aspect of the invention there is provided a method of modifying the structure of a plaque within a blood vessel, comprising: positioning a catheter apparatus in proximity to the plaque within the blood vessel; expanding an expandable membrane of a catheter apparatus with a pressure of less than 5 ATM (507 kPa); and, establishing a temperature of between +15° C. (288K) and −35° C. (238K) at an interface between the expandable membrane and the blood vessel.

Generally, the catheter apparatus may comprise a plurality of co-axial lumens. Preferably, the catheter apparatus comprises a central lumen adapted to be mounted on a standard angioplasty guide wire suitable for vascular intervention. The apparatus is preferably based on the rapid-exchange or monorail system, although over-the-wire techniques are also envisaged. Preferably, outside the central lumen, are located inlet and return lumens. Alternatively, the return lumen may be the central lumen. Preferably, outside the intermediate lumen is mounted an external lumen, which may also be referred to as a sheath. At the distal tip of the apparatus there may also be a guide member. Other lumen may be present and all the lumen may house components within themselves or between adjacent lumen.

Computer program products may also be provided for monitoring and operating the various steps of the method, receiving signals or images from or of the catheter apparatus and regulating the system either automatically or in response to user input.

According to a further aspect, there may be provided method of supplying cryoenergy to a plaque within a blood vessel to a pressure of less than 5 ATM (507 kPa) and the inside surface vessel to a temperature of between +15° C. (288K) and −35° C. (238K) such that it increases the level of collagen and the plaque is stabilized.

According to a further aspect, there may be provided a cryomedical refrigerant system using a liquid refrigerant where the liquid is infused with gaseous bubbles in suspension and where the bubbles expand and burst within the heat transfer section to create a Joule Thomson effect cooling within the liquid refrigerant.

DETAILED DESCRIPTION OF THE DRAWINGS

An example of the present invention will now be described in detail with reference to the accompanying drawings, in which.

DETAILED DESCRIPTION

Figure 1:
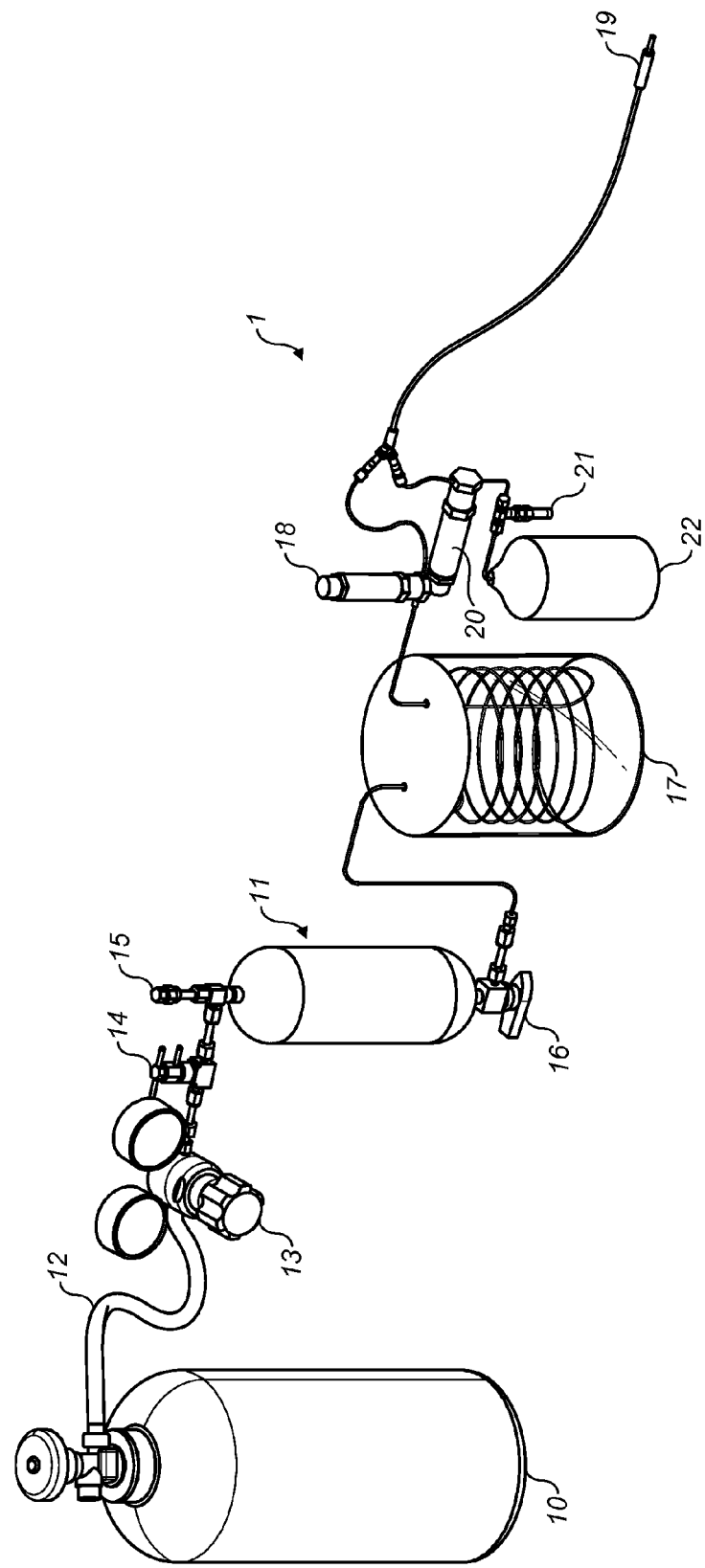
FIG. 1 shows a system for supplying cryoenergy to a target part of a vessel.

FIG. 1 is an illustration of an exemplary system for supplying cryoenergy to a target part of a vessel. It will be understood that some of the described components are not essential to the operation of the system but are described for context only. Suitable, functionally similar, or equivalent components may be used interchangeably. It is noted that throughout the present description, all pressures given as gauge pressures, that is, above atmospheric pressure.

The system 1 includes a pressure source 10, which provides pressure to the system, a fluid reservoir 11 which stores refrigerant, a heat exchanger 17 for cooling the pressurised refrigerant and a catheter 19 which is inserted into a vessel to supply cryoenergy to a target. Alternative methods of supplying cryoenergy to a vessel, without the use of a refrigerant, are contemplated and described with references to FIGS. 6a, 6b and 7 below. These include activating an endothermic reaction and controlling a thermoelectric cooling assembly such as a Peltier element.

In the illustrated system 1, the pressure source 10 is a gas pressure tank which is connected to the fluid reservoir 11. The pressure source 10 provides pressurised gas to the reservoir 11 to increase the pressure of the refrigerant stored in the reservoir 11 for passing to the heat exchanger 17. The pressure source 10 is connected to the fluid reservoir 11 with a high pressure hose coupled to a manually controlled pressure reducing regulator 13 which in turn is coupled to a bleed valve 14. The bleed valve 14 is generally closed during normal operation and may be used to vent excess pressure from the system.

Alternatively, the pressure source of the system may be a pumping arrangement such as an electric pump. In this scenario, the fluid reservoir may be unpressurised such that the pump directly provides the refrigerant to the heat exchanger at pressure from the reservoir. It is also possible to have an electric vacuum pump in the return line prior to the reservoir. This would allow for more rapid and better control of the pressure in the expandable membrane by controlling both the inlet line via the pressurization pump and the return line via the vacuum pump.

The pressure source will typically provide pressure to the system in the range of 0 to 2000 psi (13790 kPa), preferably between 100 and 1000 psi (690 kPa to 6900 kPa). The pressure required is dependent on the size and components of the system 1 and the catheter 19. The pressure may be supplied by means of a standard gear or piston pump or a gas pressure reservoir.

The fluid reservoir 11 stores the refrigerant and may be pressurised or unpressurised, as described above. In the illustrated system 1, the fluid reservoir 11 comprises a refrigerant refill port 15 and a shutoff valve 16. The refrigerant refill port 15 is provided with a cap for preventing the escape of refrigerant. Conventional equipment for transferring the refrigerant to the fluid reservoir 11 is not shown.

Connected to the fluid reservoir 11 is a chiller or heat exchanger 17. The heat exchanger 17 cools the liquid to the desired temperature before it is provided to the catheter 19. The heat exchanger 17 cools the refrigerant passing through it to a temperature cold enough to compensate for heat losses in the system 1; particularly heat lost from the connection between the heat exchanger 17 and the catheter 19.

Figure 2:
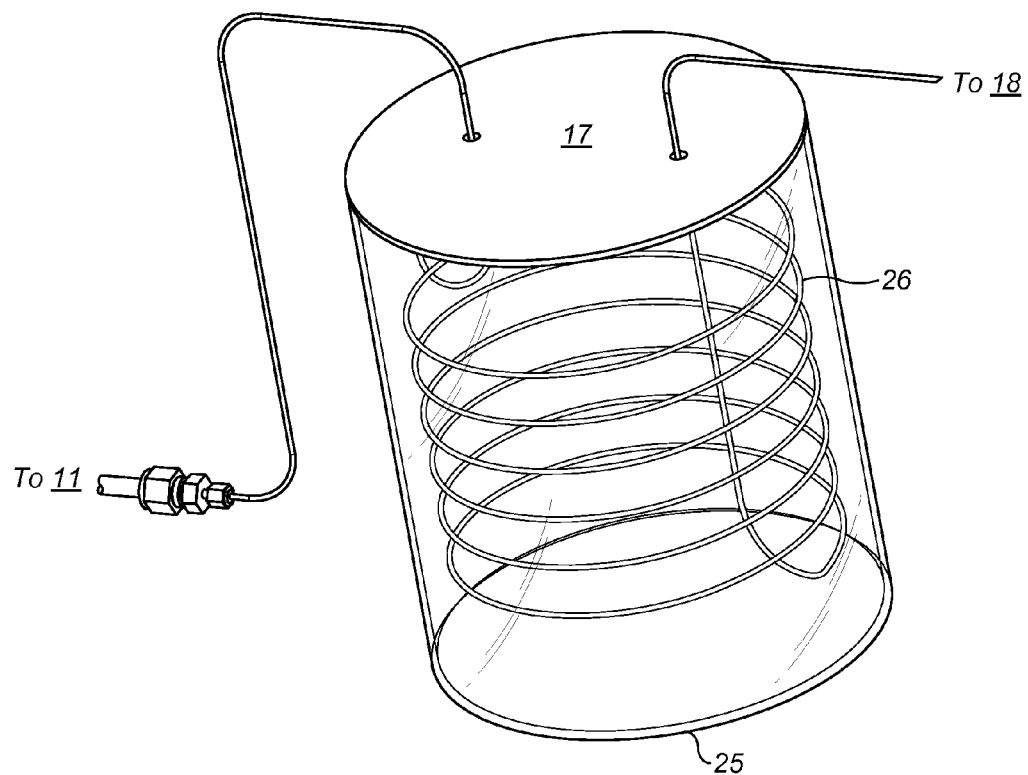
FIG. 2 shows a heat exchanger of the system.

As shown in FIG. 2, the heat exchanger 17 may be an alcohol/dry ice mixture with a coil heat exchanger to reduce the temperature of the refrigerant. A container 25 stores the mixture of alcohol and dry ice and a set of coiled tubing 26 passes through the container transporting the refrigerant through the mixture where it is cooled.

It will be understood that they are many possible implementations available to reduce the temperature of the refrigerant. For example, a common method would use standard compression-expansion refrigeration technology in a double or triple cascade to achieve the required temperature. Alternatively, a Stirling cycle device could be used.

Returning to FIG. 1, the heat exchanger 17 is coupled to a pressure transducer 18, which in turn is coupled to the catheter 19. The pressure transducer 18 measures the pressure of the refrigerant before it is provided to the catheter 19. The pressure transducer 18 is provided with wires, a power supply and meters which are not shown.

Figure 3:
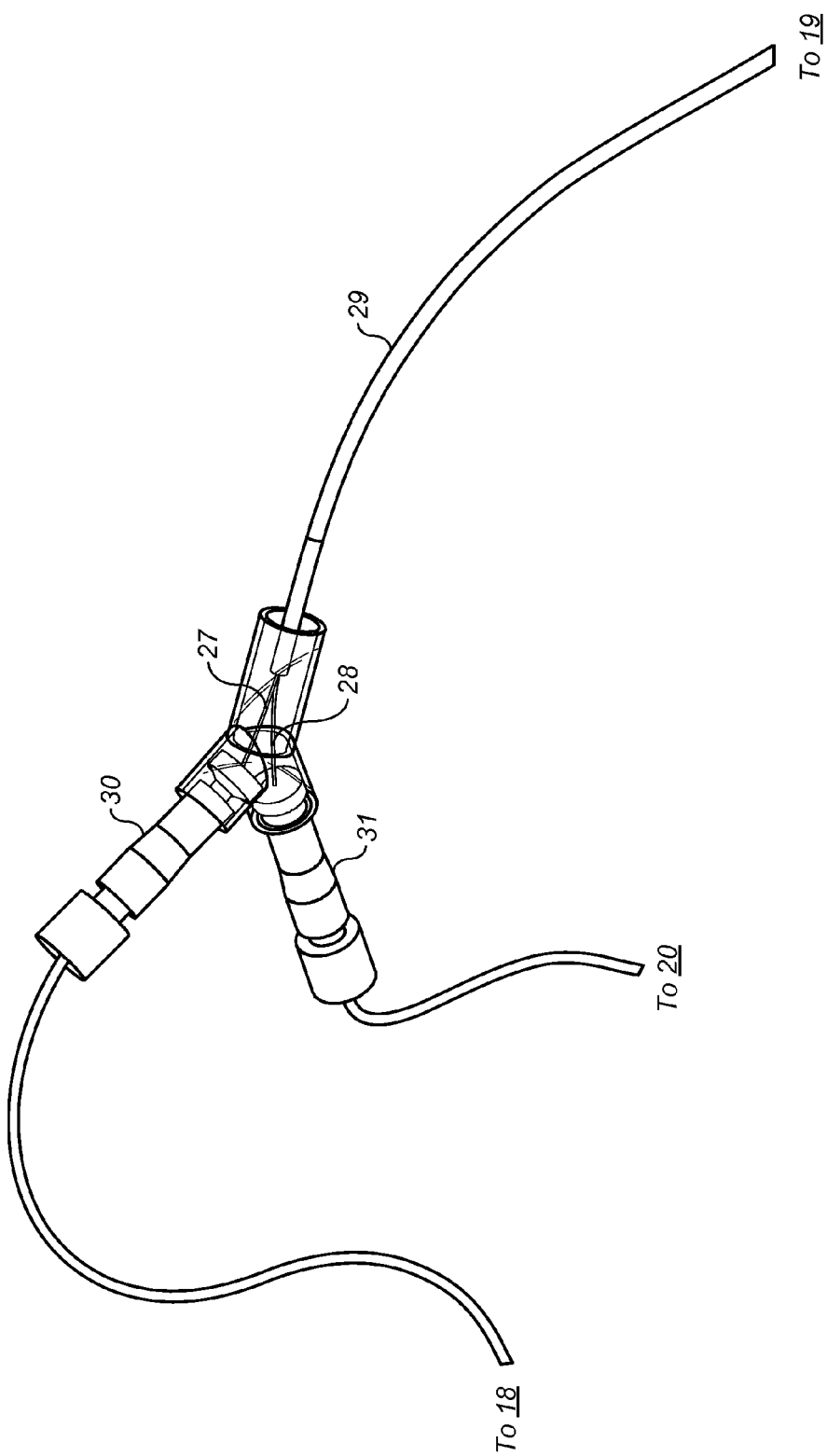
FIG. 3 shows a section of the system including inlet and return lumen.

As shown in FIG. 3, the catheter 19 has an inlet lumen 27 and a return lumen 28. These are housed within an external lumen 29. The respective sizes of lumens 27, 28 and 29 will vary depending on the specific desired pressures and flows necessary to achieve specific balloon pressures and temperatures. Lumens 28 and 29 may form a common lumen such that the return flow is carried by the external lumen. Connectors 30 and 31 serve to connect the catheter lumens to the tubes which carry the refrigerant back to the collection container 22.

Returning to FIG. 1, coupled to a return conduit of the catheter 19, which will be described in more detail below, is a second pressure transducer 20 for measuring the pressure of the refrigerant returning from the catheter 19. This is, in turn, coupled to a metering valve 21 to form a return fluid path. This metering valve or back pressure control valve 21 provides direct control over the pressure of the refrigerant in the catheter. Refrigerant is pumped to the catheter 19 and its flow is allowed or restricted by control of this valve 21 such that there is a pressure increase in the catheter 19.

A collection container 22 is coupled to the metering valve 21 to store or collect refrigerant returned from the catheter.

Figure 4:
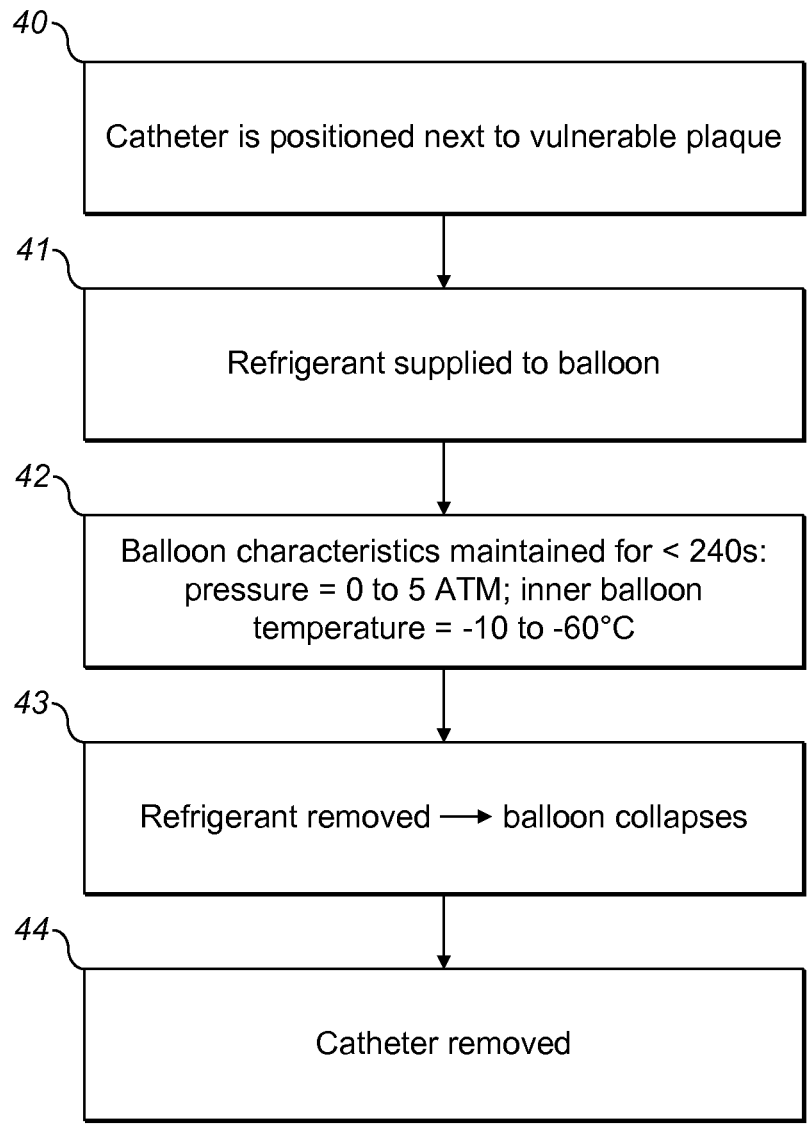
FIG. 4 shows a process of supplying cryoenergy to a target part of a vessel.

FIG. 4 is a flow chart which shows the steps carried out in supplying cryoenergy to a target vessel having a suspected vulnerable plaque or other non-critically stenosed plaque typically of less than 70%. The vessel may be an artery or vein of any part of the body such as vessels of the heart, brain, kidneys, legs, arms or neck. The catheter 19 is positioned next to a region of vulnerable plaque in a vessel (step 40). The catheter comprises a flexible heat transfer element, such as a balloon, which will be described in more detail below. Refrigerant may be provided through the inlet lumen 27 from the system 1 to the balloon which expands into thermal contact with the vulnerable plaque (step 41). Localised cooling may alternatively be provided to a balloon or other expandable membrane, such as cooling provided by a thermoelectric cooler or an endothermic reaction proximate to the expandable membrane. The pressure of the balloon, for example, the refrigerant inside the balloon or other inflation fluid inside the balloon, is maintained at less than 5 ATM (507 kPa) but may preferably be as low as 3 ATM (304 kPa) or 1 ATM (101 kPa). The temperature of the surface of the balloon is maintained between +15° C. (288K) and −35° C. (238K) and preferably between 0 to −30° C. (273K to 243K, step 42). The temperature may vary depending on the required application.

If refrigerant is used to inflate the balloon and supply cryoenergy to the vessel, the temperature of the refrigerant inside the balloon is maintained at a temperature of between −10° C. (263K) and −60° C. (213K) and preferably between −25° C. (248K) and −55° C. (218K). The inner balloon temperature will vary depending on the desired surface temperature and the balloon geometry.

Depending on the heat load there is typically a temperature difference of about 10° C. to 25° C. between inner and outer balloon temperature so that the balloon interface temperature will be between +15° C. (288K) and −35° C. (238K) when the refrigerant temperature, i.e. the inner balloon temperature, is maintained at a temperature of between −10° C. (263K) and −60° C. (213K). Similarly, the balloon tissue interface temperature will be between 0° C. (273K) and −30° C. (243K) when the refrigerant or other cooling element inside the balloon (i.e. the inner balloon temperature) is maintained between −25° C. (248K) and −55° C. (218K).

It is envisaged that the balloon is expanded into thermal contact with the plaque for a limited period of time, preferably less than 240 seconds, more preferably less than 180 seconds. In order to limit occlusion of the vessel the total time may be applied over multiple applications. Once the desired time has elapsed, the cyroenergy delivery is ceased. For example, the refrigerant may be removed from the balloon, power delivery to a thermoelectric component may be stopped, and/or an endothermic reaction may be terminated. The balloon may be collapsed and the catheter removed from the vessel (steps 43 and 44).

Two controllable variables within the system are balloon pressure and cooling element temperature and therefore tissue interface temperature. The pressure of the balloon is maintained at lower than 5 ATM (507 kPa). It may be desirable for the balloon pressure to be as low as possible for effective treatment in order to mitigate the risk of a reaction occurring in the blood vessel that leads to re-stenosis or blockage. A short-term response to the application of high-pressure cryotherapy is also often smooth muscle cell proliferation, which is potentially dangerous. The tissue interface temperature is maintained within a desired range in order to remove heat from the plaque and vessel without significantly ablating the cells.

Desirably, the cryo-treatment is applied prior to rupture of vulnerable plaque as a preventative measure. Alternatively, the cryo-treatment may be applied following a rupture to aid in stabilisation of the plaque to minimize the risk of event recurrence and to aid in healing.

Cryo-treatment of the plaque will cause the plaque morphology to change from an unstable to a more stable state such that healing is aided and a (re)occurrence of rupture and thrombus risk is reduced.

Prior work done by Tanguay et al. (2004) and Cheema et. al. (2003) has shown that intravascular cryoenergy results in a series of morphological changes which includes positive remodeling of the external elastic lamina as well as an increase in collagen formation. These changes could be positive for the purposes of plaque stabilization. In addition this work showed that cryoenergy also leads to active smooth muscle cell proliferation which could lead to negative lumen restriction and/or stenosis. This work was done at doses that were too high. Cheema et al. was done at temperatures colder than −20 C and Tanguay et al. for durations of 120 sec.

In accordance with the present invention, the same collagen formation beneficial for plaque stabilisation occurs at warmer/shorter doses while at the same time minimizing smooth muscle cell proliferation. In accordance with the present invention, the optimum dose for intravascular cryoenergy was found at temperatures when the intravascular intimal wall temperature reaches between −5 C and −20 C for a period of single 60 sec. or double 60 sec. dose with a period of at least 30 sec. between the two doses.

Figure 9:
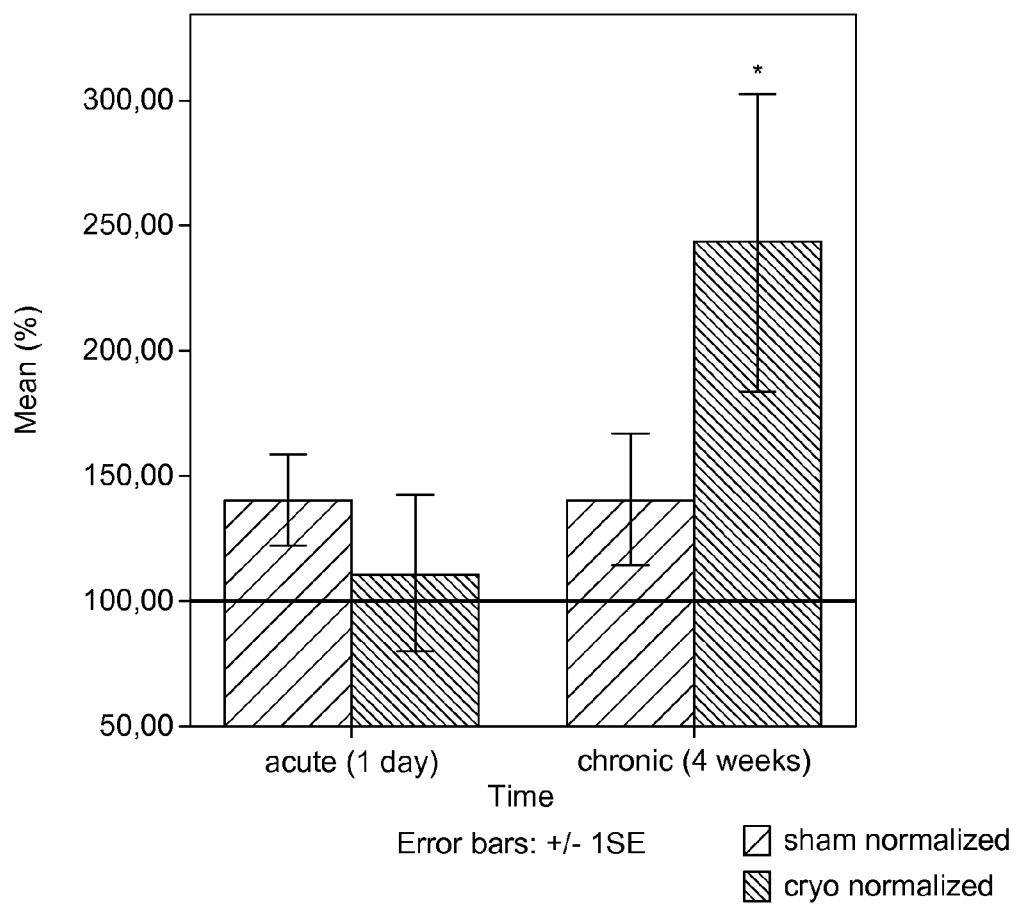
FIG. 9 shows a representation of data for normalised level of Type 1 collagen; and, FIG. 10 shows a representation of data for normalised Level of smooth muscle cells.

FIG. 9 shows a representation of the level of type I collagen 4 weeks following cryotreatment in accordance with the present invention at temperatures of between −10 C and −20 C for either a single or double 60 sec. dose is on average 200% the level acutely. This increase in collagen is statistically significant and can be beneficial as a means of stabilizing plaque.

Figure 10:
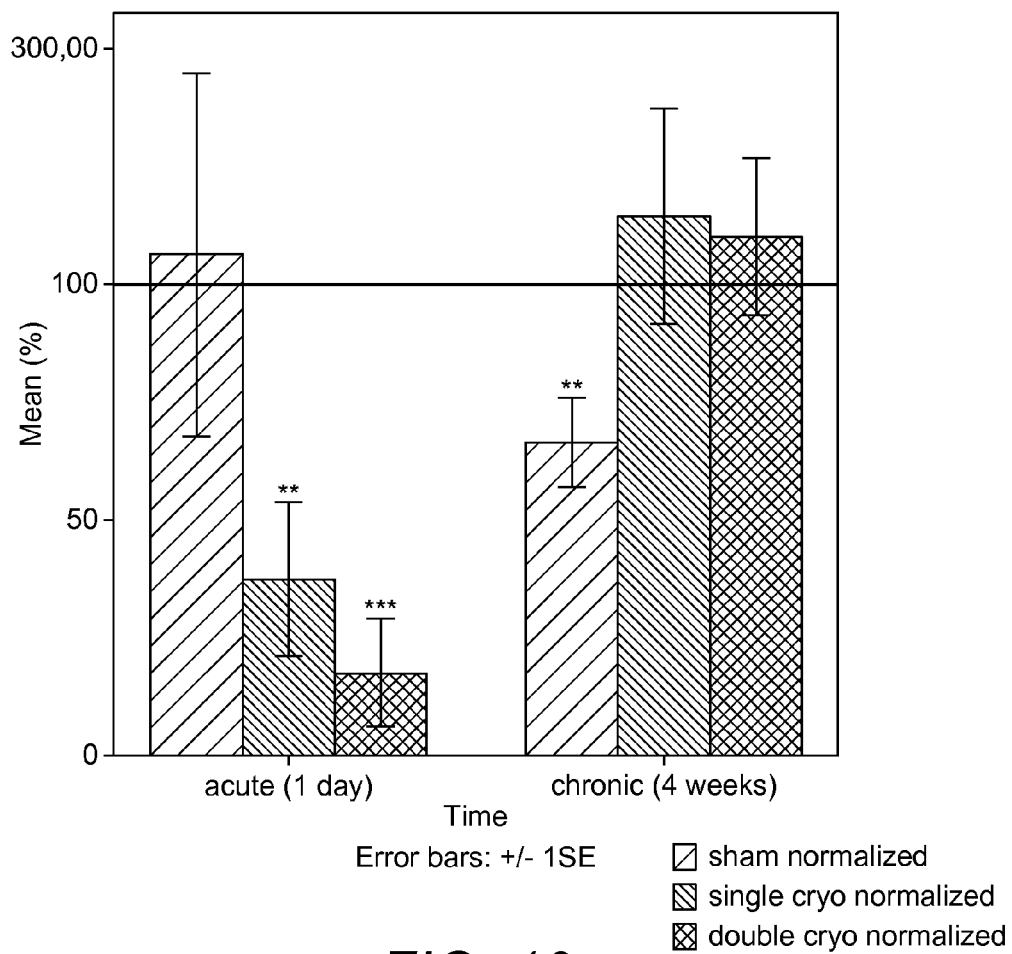

FIG. 10 from the same study shows a representation of the level of smooth muscle cell at these same cryo doses. The level of smooth muscle cells at 4 weeks for the cryotreated segments is at the same level as acutely. This demonstrates that at these doses of −10 C to −20 C and pressures of less than 5 ATM (507 kPa), in accordance with the present invention, an optimal balance is achieved between collagen production and minimization of smooth muscle cell proliferation.

Figure 5:
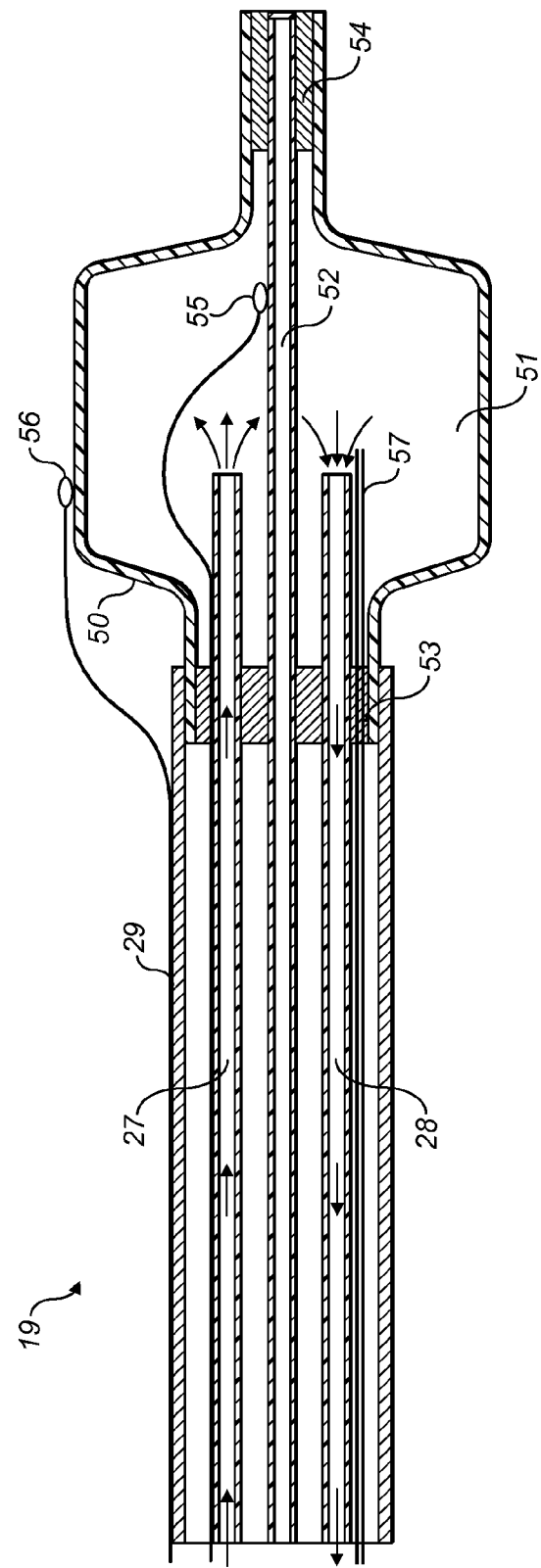
FIG. 5 shows a catheter apparatus for supplying cryoenergy to a target part of a vessel.

FIG. 5 shows an example of a catheter apparatus for use in the refrigerant based system described above. At the distal end of the catheter is a flexible heat transfer element or membrane 50 such as a balloon. The balloon 50 is inflated by the introduction of refrigerant 51. When placed in a target vessel, and inflated with refrigerant 51, the balloon will remove heat from a part of the vessel. When positioned correctly, and as described above, the balloon will desirably remove heat from unstable plaque. The balloon may be made of a variety of materials and is desirably compliant or semi-compliant to minimise damage to the vulnerable plaque and to ensure a good fit with the target area for effective heat exchange and a more even temperature distribution around the plaque. The balloon may also be non-compliant depending on the desired application. Balloon design and construction is typical of state of the art for balloon angioplasty. The balloon can be made of a variety of materials such as silicone or polyurethane for compliant balloons and nylon or polyester for non-complaint balloons. Wall thickness will also vary depending on the properties to be achieved and are generally in the range of 5 to 100 microns (0.0002" to 0.004"). Unstable plaque can occur in any region of the vasculature and balloon sizing will vary accordingly. For the coronary vasculature or below the knee peripheral applications balloon diameters will be in the range of 2.0 mm to 4.0 mm. The balloon may also have a substantially smooth exterior surface so that heat transfer is optimised from the tissue on the interior surface of the vessel and not the blood in the vessel. Balloon material and thickness may be optimised to minimize the thermal gradient across the balloon surface.

An external lumen 29 protects the inlet and return lumen 27 and 28 which transport refrigerant to and from the catheter balloon 50. The lumen 27 and 28 terminate adjacent to or within the balloon and are illustrated as spatially separate but may in fact be in a coaxial or other suitable configuration. Both the external lumen 29 and lumens 27 and 28 are flexible for insertion into a vessel and are made of suitable material. For example, the external lumen may be made of braided or unbraided PBAX and the lumen 27 and 28 may be made of nylon, polyimide, PBAX or other suitable material. The lumen may interchangeably be referred to as lumen, supply conduits or tubes throughout the present description.

Although not shown, the catheter is mounted on an angioplasty guide wire which runs through a central lumen 52 and a guide member (not shown) which defines the tip of the catheter. As in conventional catheter systems, the system may be 'over the wire' or 'rapid exchange'.

Plugs 53 and 54 are fitted at either end of the balloon to ensure that no refrigerant is allowed to escape. One of the plugs 53 may be inserted within the external lumen or at its distal end. The balloon 50 may be permanently or removably attached to the plug or the external lumen or both as long as an effective seal is maintained.

Sensors are provided within or on the balloon 50 in order to monitor the controlled variables in a feedback control system. As illustrated, a thermocouple 55 is fixed to the guidewire lumen 52 to measure the temperature inside the balloon. A second thermocouple 56 is shown attached to the external surface of the balloon in order to measure the balloon tissue interfaced temperature. In addition, a pressure sensor 57 is placed inside the balloon to accurately monitor and control the pressure within the balloon 50. The pressure sensor 57 shown is an open hydraulic tube with no flow whereby the fluid pressure inside the tube is measured outside the catheter. The pressure sensor may also be a piezoelectric transducer, fibre-optic transducer or other type of sensor. Both temperature and pressure signals can be used to control refrigerant flow such that balloon pressure and surface temperature remain within the desired ranges. The pressure transducer may also be used to detect any leaks within the catheter by sensing abnormal pressures. The temperature sensor(s) may also be used to detect vessel occlusion by the balloon.

The proximal section of the catheter (not shown) incorporates a connector for the sensors to a data interface or other signal processing unit configured to convert sensor signals into data (also not shown). The connector contains female plugs to assure proper transmittance of the electrical voltage signal transmitted from the sensors. These signals are transmitted along wires from the sensors. The wires are housed between the central lumen 52 and the inlet and return lumen 27 and 28, within the external lumen 29. The female plugs are connected to sensor wires and a common ground.

There may be more than one temperature sensor on the surface of the expandable membrane. In this manner a temperature profile or map around the expandable membrane may be determined. This could be useful in determining 'hot' or 'cold' spots which could then be used in the control of the refrigerant flow. Furthermore, one or more temperature readings, either in space or time, could be used to determine the state of blood flow between the expandable member and the vessel wall. It is known that when occlusion occurs the thermal load will greatly decrease since the blood flow ceases thereby causing a more rapid temperature drop. Since occlusion time is an important parameter to the physician and since the rate of temperature drop at a constant refrigerant flow is an indication of occlusion, the rate of temperature drop can be a useful feature to indicate when occlusion has occurred or the reverse when the vessel has been reopened following cryotreatment.

Where necessary to support extended treatment, it may be preferable for the catheter to further include a perfusion lumen to allow for the flow of blood in the vessel during treatment.

Different diameter catheters and balloon lengths may be used for different diameters of vascular tissue. It is desirable to minimise the diameter of catheters in all interventional vascular treatments.

The refrigerant used in the system is preferably in the perfluorocarbon family of liquids. For example, the 3m Novec HFE-7100 or Solvay H-Galden Z130 refrigerants may be used. Desirably, the refrigerant remains in a relatively low viscosity liquid state, preferably less than 10 cSt, over the operating temperature range of +37° C. (body temperature) to −85° C. (the approximate chiller temperature). This makes the refrigerant easier to pump at cold temperatures. The refrigerant also stays in a liquid state and is inherently safer in the case of a leak in the catheter, since the refrigerant will not vaporise and cause a gas emboli in the bloodstream. Further, the refrigerant is non-toxic and biocompatible in the case of a leak. For example, a liquid from the same class of perfluorcarbon family called 'fluosol' has been used as a synthetic blood substitute. Other refrigerants such as saline, alcohol or other biocompatible liquids may also be used.

One possible perfluorocarbon is perfluorohexane ($C_6F_{14}$) which is commonly used in medical applications and has been used as a liquid oxygen transport for liquid ventilation of burn victims. Another possible perfluorocarbon is perfluorodecalin ($C_{10}F_{18}$) which has been used as a blood substitute.

According to another embodiment of the invention the refrigerant may be infused with gaseous bubbles. These bubbles will be infused in the refrigerant prior to injection into the catheter. Several gases may be used such as nitrogen, nitrous oxide, carbon dioxide or other similar gaseous refrigerants already used in refrigerant devices. The gaseous bubbles would stay in suspension in the refrigerant until pressure is released at exit of inlet tube inside the expandable member. The pressure release would cause the bubbles to burst and result in a micro cooling effect due to the Joule Thomson effect of the rapid expansion of the gas. In this manner extra power can be achieved from the refrigerant without increasing flows or pressures of the refrigerant.

It is contemplated that radio opaque materials may be added to the refrigerant or other cooling element to provide radiopacity to the catheter in order for it to be imaged and tracked in the body. A radio opaque material may be added to the balloon or another catheter component for a similar effect. Radio opaque markers may be used to provide more specific location tracking.

Figure 6A:
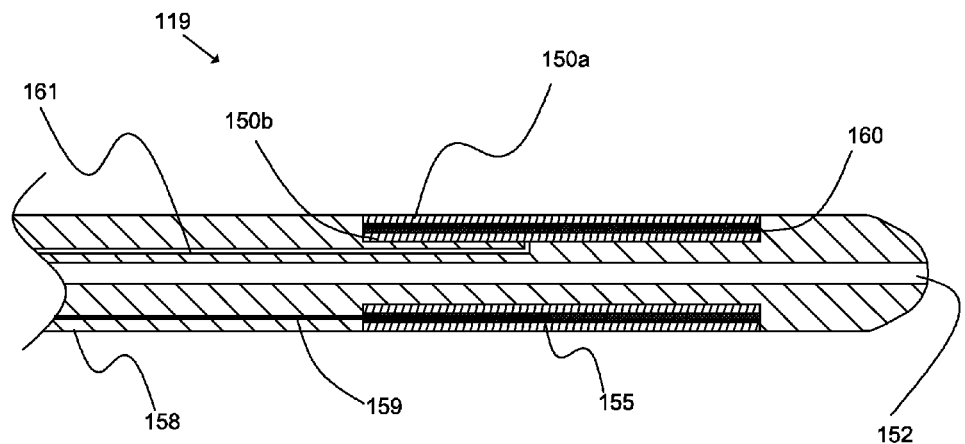
FIGS. 6a and 6b show a catheter apparatus including an endothermic reaction element for supplying cryoenergy to a target part of a vessel, and a membrane shown in unexpanded and expanded conditions, respectively.
Figure 6B:
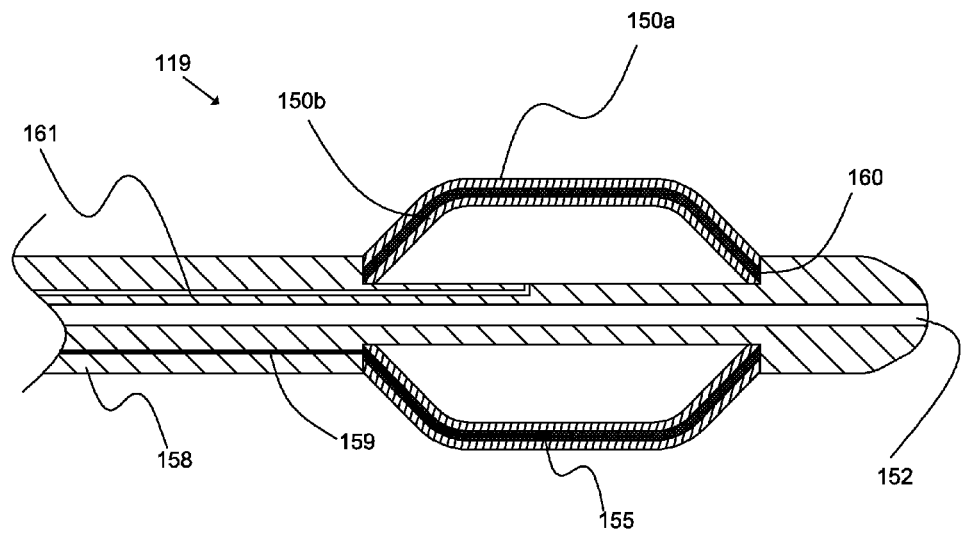

FIGS. 6a and 6b illustrate two side sectional views of the distal end of a catheter apparatus, including an endothermic reaction element and a membrane, the membrane is shown in unexpanded and expanded states in FIGS. 6a and 6b, respectively. The catheter 119 includes an elongate shaft 158, a flexible tube constructed of one or more biocompatible materials commonly used in interventional catheters, and typically including two or more lumens, as shown. The shaft 158 includes a guidewire lumen 152 configured to allow standard interventional over-the-wire vessel placement. Alternatively or additionally, the shaft 158 may include a side-car or monorail element, not shown, but positioned near the distal end of shaft 158 and including a thru' lumen configured to allow rapid exchange guidewire delivery. The shaft 158 may have an internal braid along its length or along a portion of its length, so as to support advancement through and rotation within a patient's cardiovascular system.

At the distal end of catheter 119 is a flexible heat transfer element comprising a laminate construction including an outer balloon 150a and an inner balloon 150b. Positioned between balloons 150a and 150b is a reaction element 160. The reaction element 160 comprises two or more chemicals or other agents configured to enter into or otherwise cause an endothermic reaction on demand, for example, when mixed together. An endothermic reaction occurs when two separate compounds interact to absorb energy in the form of heat. Examples of commercial devices comprising an endothermic reaction include on-demand ice packs activated by applying a twisting or compression force for mix two compounds such as water and ammonium nitrate.

The reaction element 160 further comprises a housing, such as a flexible housing, which maintains the two or more chemicals or other agents in a sealed environment, thus preventing these chemicals from entering the body of the patient. Alternatively, a single balloon 150a may be used, eliminating the inner balloon 150b.

Typically, one or more of the chemicals or other agents of the reaction element 160 are encapsulated, such as within multiple microcapsules configured to be opened when exposed to a pressure or other force. The endothermic reaction may be initiated when the balloons 150a and 150b are expanded (expanded state shown in FIG. 6b), such as by the introduction of one or more fluids such as saline through the inflation lumen 161. The inflation lumen is typically in fluid communication with one or more access ports on the proximal end of the catheter 119, such as an luer access port on a handle on the proximal end of the catheter 119. Pressure of the inserted fluid and/or expansion of the balloons 150a and 150b exert one or more compression, twisting or other forces on the reaction element 160, initiated the endothermic reaction. Alternatively or additionally, a force exerting element such as an expandable cage, might be positioned proximate to the reaction element 160. The expandable cage, not shown, may be operably connected to a trigger or other control on the proximal end of the catheter 119 and configured to apply a force such as a compression or twisting force on the reaction element 160.

In one embodiment, the one or more chemicals or other agents may be included in a slow release mechanism such as coacervates or dissolving microcapsules, so as to cause a prolonged cooling effect.

As the balloons 150a and 150b are expanded via introduction of fluid through inflation lumen 161, balloon 150a will contact a part of the target vessel, and the endothermic reaction will cause heat to be removed from the unstable plaque. Pressure within the balloon 150a is maintained below 5 ATM (507 kPa), preferably below 4 ATM (405 kPa), more preferably below 3 ATM (304 kPa), and even more preferably below 2 ATM (203 kPa). Pressure within the balloon 150a may also be maintained at a level less than or approximately equal to 1 ATM (101 kPa). With these reduced pressure levels, the risk of plaque rupture and subsequent stenosis when cryoenergy is applied to vulnerable plaque is significantly reduced while modifying plaque structure through the supply of cryoenergy such that it is stabilized or eliminated. The balloon 150a and/or balloon 150b may be inflated through the use of a commercially available endoflator, not shown, but attached to be in fluid communication with the inflation lumen 161.

Numerous pairs or groups of chemicals can be used to cause an endothermic reaction when exposed to each other. The reaction element 160 may include endothermic reaction element combinations selected from the group comprising: water and ammonium nitrate; water and ammonium chloride; barium hydroxide octahydrate crystals and dry ammonium chloride; water and ammonium chloride; thionyl chloride and cobalt(II) sulphate heptahydrate; water and potassium chloride; water and ammonium thiocyanate; ethanoic acid and sodium carbonate; and combinations of these. Once the endothermic reaction is initiated, the area proximate to the balloon 150a is cooled, as described with the use of refrigerant above. An endothermic reaction between appropriate chemicals (e.g. water and ammonium nitrate) can be configured to achieve cool temperatures rapidly. Typically, the reaction element 160 comprises both water and ammonium nitrate in separate tubes. When these tubes are broken, the water and ammonium nitrate mix, setting off an endothermic reaction and causing the water to freeze. The freezing of the water prevents all of the ammonium nitrate from instantaneously mixing with the water. As the ice melts, the water mixes with additional ammonium nitrate, causing additional endothermic reactions and forcing the melted ice to re-freeze. This process allows the reaction element 160 to remain frozen and maintain extremely low temperatures for an extended period of time, despite being maintained prior to activation at room or body temperature.

The reaction element 160 and catheter 119 are configured to maintain the temperature on the exterior surface of balloon 150*a* to a target value or range of values. The reaction element 160 and catheter 119 may be configured to maintain a temperature between −35° C. (238K) and +15° C. (288K), preferably between −30° C. (243K) and 0° C. (273K).

The balloons 150*a* and 150*b* may be constructed of compliant, semi-compliant or non-compliant materials as described above. The balloon 150*a* may have a substantially smooth exterior surface so that head transfer is optimised from the tissue on the interior surface of the vessel and not the blood in the vessel.

Sensors may be provided proximate to the balloon 150*a*, reaction element 160 and/or balloon 150*b*, so as to monitor the temperature proximate to the balloon 150*a*. As illustrated, a thermocouple 155 may be positioned within the reaction element 160. One or more additional thermocouples. not shown, may be included at different locations. The thermocouple 155 is connected to wires 159 which travel proximally and electrically connect to an electronic assembly, not shown, but typically a data interface as described above configured to determine the temperature at thermocouple 155 based on signals received from thermocouple 155.

The measured temperature may be used to confirm proper temperature for the procedure, triggering an alarm if the temperature is out of a predetermined range. Alternatively, the measured temperature may be used to adjust the endothermic reaction in a closed loop configuration, such as by causing more or less chemicals to be combined, for example, by applying more or less force to microcapsules includes one or more chemicals. A pressure sensor, also not shown but similar to the pressure sensors described above, may be placed inside the balloon 150*b* to accurately monitor and control the pressure within the balloon 150*a* and/or 150*b*. The pressure transducer may also be used to detect any leaks within the catheter 119, such as by sensing abnormal pressures.

Where necessary to support extended treatment, it may be preferable for the catheter to further include a perfusion lumen to allow for the flow of blood in the vessel during treatment. Different diameter catheters and balloon lengths may be used for different diameters of vascular tissue. One or more portions of the catheter 119 may be radiopaque and/or include a radiopaque marker.

The catheter 119 may be part of a system (system components not shown), such as a system including a handle comprising one or more controls and/or a user interface such as a graphical user interface. The system may include a computer so that the system may be software controlled. The system may include assemblies used to perform closed loop therapy such as closed loop temperature and/or pressure monitoring based on signals received from one or more sensors of the catheter 119.

Figure 7:
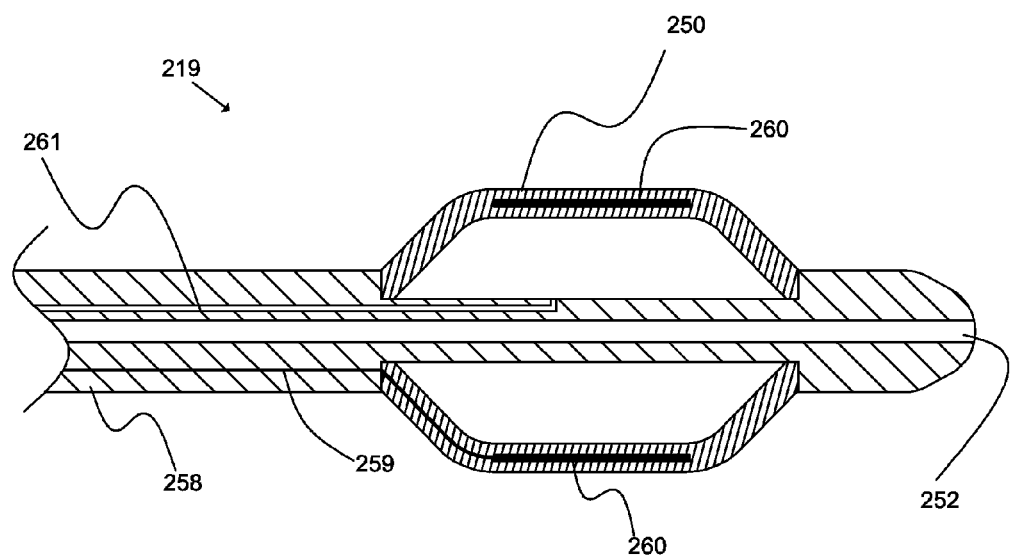
FIG. 7 shows a catheter apparatus including a thermoelectric cooler for supplying cryoenergy to a target part of a vessel and a membrane shown in an expanded condition.

FIG. 7 illustrates a side sectional view of the distal end of a catheter apparatus, including a thermoelectric cooling element and a membrane. The membrane is shown in its expanded state. The catheter 219 includes an elongate shaft 258, a flexible tube constructed of one or more biocompatible materials, and typically includes two or more lumens as shown. The shaft 258 includes a guidewire lumen 252 configured to allow standard interventional over-the-wire vessel placement. Alternatively or additionally, the shaft 258 may include a side-car or monorail element, not shown, but positioned near the distal end of the shaft 258 and including a thru' lumen configured to allow rapid exchange guidewire delivery. The shaft 258 may have an internal braid along its length or along a portion of its length. At the distal end of the catheter 219 is a flexible heat transfer element, a cooling element 260, comprising a tubular structure and positioned within the wall of the balloon 250. The cooling element 260 typically traverses a majority of the length of the balloon 250 intended to contact the wall of a vessel. The cooling element 260 typically comprises a peltier cooler, or other suitable thermoelectric cooling element. A peltier cooler, known to those of skill in the art, creates a heat flux between the junction of two different types of materials. The cooling element 260 is typically a solid-state active heat pump which transfers heat from one side to its other against the temperature gradient, with consumption of electrical energy. The cooling element 260 is electrically connected to wires 259 which travel proximally, and typically connect, via a handle, to a power supply such as a battery (handle and battery supply not shown). The cooling element 260 may include a tube comprising multiple hinged, rigid sections, such that the cooling element 260 may be constrained in a radially compact state as the balloon 250 is deflated, for example, by applying a vacuum through the lumen 261 to the balloon 250. Alternatively, the cooling element 260 may be constructed of a flexible material configured to radially compress as the balloon 250 is deflated.

Typically, power can be applied, for example, by an operator of catheter 219, to the cooling element 260, when the balloon 250 is expanded (expanded state shown in FIG. 7). Expansion of the balloon 250 is caused by the introduction of one or more fluids such as saline through the inflation lumen 261. The inflation lumen is typically in fluid communication with one or more access ports on the proximal end of the catheter 219, such as an luer access port on a handle on the proximal end of the catheter 219. The catheter 219 may include means of extracting heat from the inner surface of the cooling element 260. Heat extraction may be accomplished by circulating fluid past the inner surface of the cooling element 260, such as by circulating the inflation fluid passed into the balloon 250 via the lumen 261. Additional fluid delivery lumens, not shown, may be included to create the proper flow of the heat extracting fluid proximate the inner surface of the cooling element 260.

As the balloon 250 is expanded via introduction of fluid through the inflation lumen 261, the balloon 250 will contact a part of the target vessel, and the endothermic reaction will cause heat to be removed from the unstable plaque. Pressure within the balloon 250 is maintained below 5 ATM (507 kPa), preferably below 4 ATM (405 kPa), more preferably below 3 ATM (304 kPa), and even more preferably below 2 ATM (203 kPa). Pressure within balloon 250 may be maintained at a level less than or approximately equal to 1 ATM (101 kPa). With these reduced pressure levels, the risk of plaque rupture and subsequent stenosis when cryoenergy is applied to vulnerable plaque is significantly reduced while modifying plaque structure through the supply of cryo energy such that it is stabilized or eliminated. The balloon 250 may be inflated through the use of a commercially available endoflator or by controlling of a fluid pump inside the console, not shown, but attached to be in fluid communication with the inflation lumen 261.

The balloon 250 may be constructed of compliant, semi-compliant or non-compliant materials as described above. The balloon 250 may have a substantially smooth exterior surface so that heat transfer is optimised from the tissue on the interior surface of the vessel and not the blood in the vessel.

Sensors, not shown but described in detail above, may be provided proximate to the balloon 250 and/or cooling element 260 so as to monitor the temperature proximate to the balloon 250. A thermocouple proximate to the balloon 250 is electrically connected to an electronic assembly, also not shown, but typically a data interface or other sensor monitoring assembly as described above. The measured temperature may be used to confirm proper temperature for the procedure, triggering an alarm if the temperature is out of a predetermined range. Alternatively or additionally, the measured temperature may be used to adjust the cooling effect reaction in a closed loop configuration, such as by altering the power delivered to the cooling element 260. A pressure sensor, also not shown but similar to the pressure sensors described above, may be placed inside the balloon 250 to accurately monitor and/or control the pressure within the balloon 250. The pressure transducer may also be used to detect any leaks within the catheter 219 by sensing abnormal pressures.

Where necessary to support extended treatment, it may be preferable for the catheter to further include a perfusion lumen to allow for the flow of blood in the vessel during treatment. Different diameter catheters and balloon lengths may be used for different diameters of vascular tissue. It is desirable to minimise the diameter of catheters in all interventional vascular treatments. One or more portions of the catheter 219 may be radiopaque and/or include a radiopaque marker.

The catheter 219 may be part of a system (system components not shown), such as a system including a handle comprising one or more controls and/or a user interface such as a graphical user interface. The system may include a computer, such that the system may be software controlled. The system may include assemblies used to perform closed loop therapy such as closed loop temperature and/or pressure monitoring based on signals received from one or more sensors of the catheter 219.

Figure 8:
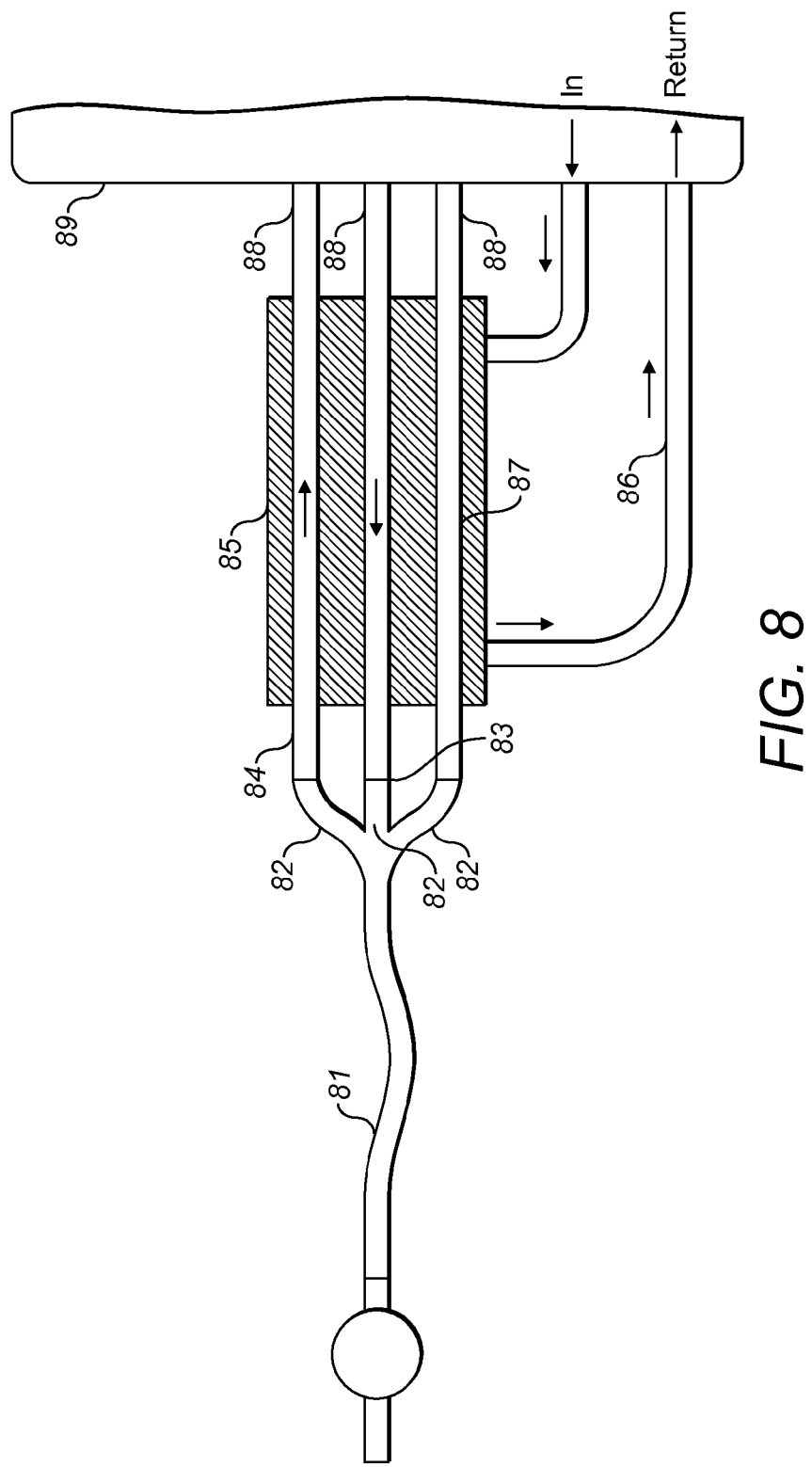
FIG. 8 shows an exemplary connector assembly apparatus.

FIG. 8 illustrates an exemplary connection apparatus between the catheter 81 and the refrigerant supply console 89. This connection apparatus 85 may incorporate all the necessary hydraulic and electrical connections. For example, this apparatus 85 may include the temperature and pressure sensor wires 87, the inlet 83 and return 84 lumen and possibly other sensor tubes or wires that may be incorporated into the system. Connectors 82 may be provided between the catheter apparatus and the connection apparatus. Further connectors 88 may between the connector assembly apparatus 85 and the cryorefrigerant supply console 89. In one embodiment (not shown) the inlet line of the connection is located coaxially inside the return line in order to minimize heat loss from the inlet line. Also shown in FIG. 8 is a separate heat exchanger with a refrigerant line 86 supplied by the refrigerant console and returning to the console 89 that may be used to further cool the hydraulic lines in the connector apparatus as a method to minimize heat losses in the connector apparatus 85. The heat exchanger may be a stand-alone rigid component or can be a flexible component that is integrated within the connection apparatus.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth hereinbelow not be construed as being order-specific unless such order specificity is expressly stated in the claim.

What is claimed is:

1. A method of supplying cryoenergy to a plaque within a blood vessel, comprising:
   expanding a single expandable membrane of a catheter apparatus using a liquid to less than 5 ATM (507 kPa), the catheter apparatus having been placed in thermal contact with the plaque within the blood vessel; and,
   establishing a temperature of between +15° C. (288K) and −35° C. (238K) at an interface of the expandable membrane and the blood vessel.

2. A method according to claim 1, wherein the expandable membrane is compliant with the blood vessel.

3. A method according to claim 1, wherein the expandable membrane is semi-compliant with the blood vessel.

4. A method according to claim 1, wherein the expandable membrane is non-compliant with the blood vessel.

5. A method according to claim 1, wherein the expandable membrane has a substantially smooth exterior surface.

6. A method according claim 1, further comprising determining expandable membrane characteristics using a sensor provided with the catheter apparatus.

7. A method according to claim 1, further comprising imaging the catheter apparatus, wherein the expandable membrane comprises a radio opaque substance.

8. A method according claim 1, wherein the expandable membrane is expanded with a pressure of less than 4 ATM (405 kPa).

9. A method according to claim 8, wherein the expandable membrane is expanded with a pressure of less than 3 ATM (304 kPa).

10. A method according to claim 9, wherein the expandable membrane is expanded with a pressure of less than 2 ATM (203 kPa).

11. A method according to claim 10, wherein the expandable membrane is expanded with a pressure of less than or approximately equal to 1 ATM (101 kPa).

12. A method according to claim 1, wherein the expandable membrane is configured to contain refrigerant and wherein the act of establishing a temperature comprises supplying refrigerant to the expandable membrane.

13. A method according to claim 12, wherein refrigerant inside the expandable membrane is maintained in a liquid state.

14. A method according to claim 13, wherein the refrigerant has a boiling point at atmospheric pressure above +37° C. (310K), a freezing point at atmospheric pressure below −85° C. (358K) and a dynamic viscosity at −85° C. (188K) of below 10 cSt (10×10−6 m2/s).

15. A method according to claim 12, wherein refrigerant inside the expandable membrane is maintained at a temperature of between −25° C. (248K) and −55° C. (218K).

16. A method according to claim 12, wherein the refrigerant comprises a perfluorocarbon.

17. A method according to claim 12, further comprising determining refrigerant characteristics using a sensor provided with the catheter apparatus.

18. A method according to claim 1, wherein the temperature within the expandable membrane is maintained by a cooling element positioned proximate to the expandable membrane.

19. A system comprising:
- a catheter apparatus, the catheter apparatus having a single expandable membrane;
- a pressure control system configured to regulate the expansion of the expandable membrane using a liquid such that the expandable membrane is expanded with a pressure of less than 5 ATM (507 kPa); and,
- a cooling element configured to establish a temperature of between +15° C. (288K) and −35° C. (238K) at an interface between the expandable membrane and a blood vessel when the catheter apparatus has been placed in the blood vessel; and
- a temperature control system configured to monitor temperature at the interface and adjust the cooling element to maintain the interface temperature between +15° C. (288K) and −35° C. (238K).

20. A system according to claim 19, wherein the cooling element is selected from the group consisting of: a refrigerant; endothermic reaction components; a thermoelectric cooler; and combinations thereof.

21. A system according to claim 19, wherein the expandable membrane is configured to contain fluid, the system further comprising a fluid supply for supplying fluid to the expandable membrane and wherein the pressure control system is configured to regulate the pressure of the fluid supply such that the expandable membrane is expanded with a pressure of less than 5 ATM (507 kPa).

22. A system according to claim 21, further comprising a vacuum pump positioned in a return line between the expandable membrane and a fluid reservoir.

23. A system according to claim 19, further comprising a connection apparatus adapted to cool a refrigerant supply line by a separate refrigerant line from the fluid supply.

* * * * *